United States Patent [19]

Schlak et al.

[11] 4,202,831
[45] May 13, 1980

[54] PREPARATION OF SILANES

[75] Inventors: Ottfried Schlak, Leverkusen; Hans-Heinrich Moretto, Cologne, both of Fed. Rep. of Germany

[73] Assignee: Bayer Aktiengesellschaft, Leverkusen, Fed. Rep. of Germany

[21] Appl. No.: 15,375

[22] Filed: Feb. 26, 1979

[30] Foreign Application Priority Data

Mar. 17, 1978 [DE] Fed. Rep. of Germany ....... 2811854

[51] Int. Cl.² .............................................. C07F 7/18
[52] U.S. Cl. .................................... 556/467; 556/451
[58] Field of Search .................................. 260/448.2 P

[56] References Cited

U.S. PATENT DOCUMENTS

| | | | |
|---|---|---|---|
| 2,745,860 | 5/1956 | Bailey | 260/448.2 P |
| 3,008,975 | 11/1961 | Schubert | 260/448.8 R |
| 3,398,177 | 8/1968 | Stewart | 260/448.2 P |
| 3,567,756 | 3/1971 | Rothe | 260/448.8 R |
| 3,646,088 | 2/1972 | Bakassian et al. | 260/448.2 P |
| 3,651,117 | 3/1972 | Bennett | 260/448.8 R |
| 3,718,682 | 2/1973 | Bakassian et al. | 260/448.2 P |
| 3,806,549 | 4/1974 | Foley | 260/448.8 R |
| 4,016,188 | 4/1977 | Kötzsch et al. | 260/448.8 R |
| 4,060,538 | 11/1977 | Kötzsch et al. | 260/448.8 R |
| 4,070,386 | 1/1978 | Rossmy | 260/448.8 R |

FOREIGN PATENT DOCUMENTS 1162365 2/1964 Fed. Rep. of Germany .
2033373 4/1971 Fed. Rep. of Germany .
50-84094 10/1975 Japan .
0653237 5/1951 United Kingdom .

OTHER PUBLICATIONS

Noll, "Chemie und Technologie der Silicone," Winheim (1968), p. 78.

Primary Examiner—Paul F. Shaver
Attorney, Agent, or Firm—Sprung, Felfe, Horn, Lynch & Kramer

[57] ABSTRACT

A process for the preparation of a silane of the formula $$R_a SiH_b(OR')_{4-(a+b)}$$

wherein
R is optionally substituted alkyl, alkenyl or aryl with up to 7 C atoms,
R' is alkyl with 1 to 4 C atoms,
a and b each independently is 1, 2 or 3, and
a+b is at most 4, comprising reacting an Si-H polysiloxane with a compound of the formula $$R_a Si(OR')_{4-a}$$

in the presence of a conventional redox-stable siloxane polymerization catalyst which favors the exchange reaction. Advantageously the catalyst is AlCl₃ and R and R' are methyl, ethyl, vinyl or phenyl.

3 Claims, No Drawings

PREPARATION OF SILANES

The present invention relates to a process for the preparation of silanes of the general formula $$R_a SiH_b (OR')_{4-(a+b)} \quad (I)$$

wherein
R represents an optionally substituted alkyl, alkenyl or aryl radical with up to 7 C atoms,
R' represents an alkyl radical with 1–4 C atoms and
a and b represent 1, 2 or 3 and the sum of a+b is at most 4,
by reaction of organopolysiloxanes, containing Si-H groups, with compounds of the general formula $$R_a Si(OR')_{4-a}$$

wherein
R, R' and a have the abovementioned meanings, in the presence of redox-stable siloxane polymerization catalysts which are in themselves known and which favor the exchange reaction.

Silanes of the general formula I are in general obtained by reacting halogenosilanes of the formula $$R_a SiH_b X_{4-(a+b)} \quad (X = Br, Cl)$$

with alcohols (compare, for example, V. Bazant, Organosilicon Compounds (1965), page 125).

However, frequently only unsatisfactory yields are achieved in this reaction. The reason for this is mainly that the hydrogen chloride formed destroys both the silicon-alkoxy group, giving the alcohol and the chlorosilane and also (particularly in the presence of alcohol) destroys the hydrosilane bond, with elimination of hydrogen and formation of a

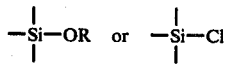

bond. Furthermore, the hydrogen chloride forms, with the alkanols employed, chloroalkanes and, transiently, water which in its turn hydrolytically attacks the chlorosilanes and alkoxysilanes.

These side reaction can largely be suppressed if the hydrogen chloride is rapidly removed from the reaction mixture or is trapped by means of bases. However, this requires complicated apparatus and complicated measures.

Thus, for example, the use of an acid acceptor is described in DT-AD (German Published Specification) 1,162,365 and in DT-AS (German Published Specification) 2,304,503; the use of reduced pressure is described in U.S. Pat. No. 3,008,975; the use of pentane is described in U.S. Pat. No. 3,806,549; the reaction in the vapor phase is described in DT-OS (German Published Specification) 2,144,748; the use of a jacketed tube is described in DT-OS (German Published Specification) 2,033,373 and the use of an inert gas and low temperatures is described in DT-AS (German Published Specification) 1,298,972.

Furthermore, it is known to circumvent the side reactions described above by converting trimethylchlorosilane into trimethylethoxysilane, as described in British Pat. No. 653,237, and reacting the latter with methylhydrogenodichlorosilane in accordance with the following equation:

$$2\ Me_3SiOEt + MeHSiCl_2 \rightarrow 2\ Me_3SiCl + MeHSi(OEt)_2.$$

The trimethylchlorosilane formed as a by-product is at the same time continuously distilled from the equilibrium. Furthermore, Japanese Patent Application 084,094 describes a controlled elimination of hydrogen in accordance with the equation:

$$RSiH_3 + 2\ R'OH \rightarrow RHSi(OR')_2 + 2\ H_2.$$

A further process, which however is also expensive, is to react triethyl orthoformate with methylhydrogenodichlorosilane (compare, for example, W. Noll, Chemie und Technologie der Silicone (Chemistry and Technology of the Silicones), Weinheim 1968, page 78).

However, all the processes mentioned have some disadvantages which make them unsuitable for industrial use.

Surprisingly, it has now been found that, according to the invention, silanes of the formula $$R_a SiH_b (OR')_{4-(a+b)}$$

can be obtained in a simple manner, and with good yields, if the alkylhydrogenopolysiloxanes, which in each case are readily available, are reacted, in the presence of a catalyst, with the appropriate alkoxysilanes, which are also readily available, so that the difficulties described above do not arise. In this reaction, one or more alkoxy groups of the monomeric silane undergo exchange with a hydrogen atom, bonded directly to the silicon atom, of the alkylhydrogenopolysiloxane. At the same time, polysiloxanes in which the Si-H hydrogen is partially or completely replaced by alkoxy groups, are formed.

Suitable alkylhydrogenopolysiloxanes for the process according to the invention are those of the general formula

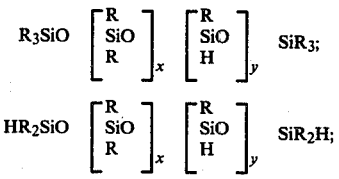

wherein
R has the abovementioned meaning, and
x can be 0 to 500 and
y can be 2 to 500, preferably 3 to 70.

The commercially available methylsiloxanes are preferred, but other siloxanes, such as, for example, also phenylsiloxanes, ethylsiloxanes, vinylsiloxanes and mixtures of these, are suitable as well. Halogen and/or $C_{1-4}$-alkyl or -alkoxy substituents may also be present, e.g. chloromethylsilanes.

Furthermore, polymers can be employed as the starting substance, such as, for example,

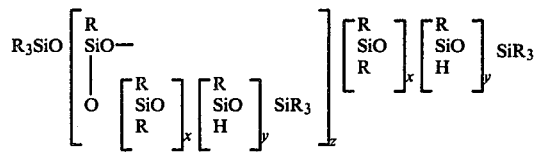

wherein

R, x and y independently of one another have the above meanings and z is 0-10, or cyclic compounds such as

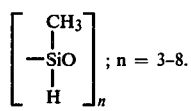

The reaction takes place in the presence of siloxane polymerization catalysts which are in themselves known and are redox-stable under the particular reaction conditions.

Examples of suitable catalysts are alkali metals, such as sodium, their alcoholates and hydroxides, such as sodium methylate and potassium hydroxide, tert.-amines, strong acids, bleaching earths and metal halides, such as, for example, $AlCl_3$, or other compounds, such as, for example, Al acetylacetonate. Further suitable catalysts are described in W. Noll, loc. cit., page 81 and 188-197, the disclosure of which is incorporated herein by reference.

The preparation according to the invention can be carried out in a simple manner in a conventional reaction vessel; the temperature in the reaction vessel must be selected so that the desired reaction product distils off rapidly. Reduced pressure or, where appropriate, excess pressure can also be used for this purpose. As a rule, however, the preparation is carried out under normal pressure. The reaction temperature is about 30° C. to 300° C., in particular about 100° C. to 250° C. It proves advantageous to carry out the reaction bhy initially mixing a part of the alkoxysilane with the catalyst, metering in the remaining reaction mixture and distilling off the reaction product at the rate at which it is formed; however, other ways of conducting the reaction are also possible. The amount of the catalyst can be varied in accordance with the desired rate of reaction; the range of about 0.1 to 10% by weight, relative to the starting compounds, has however proved advantageous. About 0.5-5% by weight is particularly preferred.

Furthermore, it can be advantageous, for the purpose of reducing the viscosity, to work in an inert solvent of which the boiling point is higher than that of the desired product, such as, for example, to carry out the reaction in toluene or xylene.

The examples which follow are intended further to illustrate the process according to the invention. Percentage data are percentage by weight data, unless stated otherwise. The abbreviations Me and Et represent $CH_3$ and $C_2H_5$—respectively; M represents a $(CH_3)_3SiO$—group and D represents a —$(CH_3)SiO$—group.

EXAMPLE 1

10 g of $AlCl_3$ (1.0%) and 100 g of $CH_3Si(OC_2H_5)_3$ (0.56 mol) were initially introduced into a 1 1 three-necked flask equipped with a thermometer, magnetic stirrer, dropping funnel, mirror-coated column (80 cm long, 8 cm diameter, 6 mm Raschig ring packing), distillation head and bubble counter at the apparatus outlet. The apparatus was flushed thorougly with dry $N_2$; the material in the flask was then heated to 140° C. and a mixture of 606 g of $CH_3Si(OC_2H_5)_3$ (3.4 mols) and 307 g of methylhydrogenopolysiloxane of the formula $(CH_3)_3Si-O[HCH_3SiO]_{30}Si(CH_3)_3$ (about 4.7 mols of SiH) was then added dropwise over the course of 5 hours. At the same time, a distillate was taken off, at the rate at which it was formed, at a boiling point of between 95 and 103° C.; according to analysis by gas chromatography, this distillate contained 94.4% of $HCH_3Si(OC_2H_5)_2$. 497 g of distillate were obtained (3.49 mols of $HCH_3Si(OC_2H_5)_2$ or 88% relative to $CH_3Si(OC_2H_5)_3$). The bottom temperature rose, during this time, to 210° C. The apparatus was then flushed with $N_2$ until it had cooled. 507 g of a mobile liquid remain; according to analysis by NMR spectroscopy, this liquid had the approximate composition

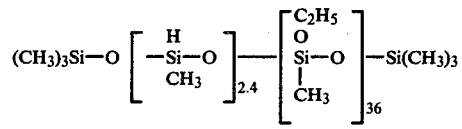

EXAMPLE 2

756 g of $MeSi(OEt)_3$ (4.24 mols), 20 g of $AlCL_3$ (1.88%) and 307 g of a methylhydrogenopolysiloxane of the formula $MD_{11}{}^HM$ (4.1 mols of SiH) were reacted in the same manner as in Example 1.

In this reaction, a distillate was obtained which according to analysis by gas chromatography consisted of 89.3% of $MeHSi(OEt)_2$. 590 g of distillate were obtained (3.92 mols of $MeHSi(OEt)_2$ or 95.7% relative to SiH employed).

475 g of a mobile liquid remained; according to analysis by NMR spectroscopy, the liquid had the approximate composition $MD_{18}{}^{OET}M.$

EXAMPLE 3

626 g of $MeSi(OEt)_3$ (2.95 mols), 10 g of aluminum acetylacetonate (1.3%) and 232 g of a methylhydrogenopolysiloxane of the formula $MD_{11}{}^HM$ (3.1 mols of SiH) were reacted in the same manner as in Example 1. In this reaction, a distillate was obtained which according to analysis by gas chromatography consisted of 66.4% of $MeHSi(OEt)_2$. 346 g of distillate were obtained (1.71 mols of $MeHSi(OEt)_2$ or 55.2% relative to SiH employed). 409 g of a mobile liquid remained; according to analysis by NMR spectroscopy, the liquid had the approximate composition $MD_{23}{}^{OEt}M$.

EXAMPLE 4

353 g of $MeSi(OEt)_3$ (1.98 mols), 2.5 g of KOH (0.5%) and 154 g of a methylhydrogenopolysiloxane of the formula $MD_{11}{}^HM$ (2.06 mols of SiH) were reacted in the same manner as in Example 1. The yield of MeHSi(OEt)$_2$, according to analysis by gas chromatography, was 32.1%, relative to SiH.

EXAMPLE 5

180 g of MeSi(OEt)$_3$ (1.01 mols), 15.2 g of tributylamine (6.1%) and 70 g of a methylhydrogenopolysiloxane of the formula MD$_{54}{}^H$M (1.1 mols of SiH) were reacted in the same manner as in Example 1. The yield of MeHSi(OEt)$_2$, according to analysis by gas chromatography, was 13.2% relative to SiH.

EXAMPLE 6

180 g of MeSi(OEt)$_3$ (1.01 mols), 2 g of C$_4$F$_9$SO$_3$H (0.8%) and 70 g of a methylhydrogenopolysiloxane of the formula MD$_{54}{}^H$M (1.1 mols of SiH) were reacted in the same manner as in Example 5. The yield of MeHSi(OEt)$_2$, according to analysis by gas chromatography, was 68.4%, relative to SiH.

EXAMPLE 7

180 g of MeSi(OEt)$_3$ (1.01 mols), 25 g (10%) of bleaching earth and 70 g of a methylhydrogenopolysiloxane of the formula MD$_{54}{}^H$M (1.1 mols of SiH) were reacted in the same manner as in Example 5. The yield of MeHSi(OEt)$_2$, according to analysis by gas chromatography, was 33.9%, relative to SiH.

EXAMPLE 8

520 g of Me$_2$Si(OEt)$_2$ (3.51 mols), 37.5 (5.0%) of AlCl$_3$ and 230 g of a methylhydrogenopolysiloxane of the formula MD$_{30}{}^H$M (3.51 mols of SiH) were reacted in the same manner as in Example 1.

In this reaction, a distillate was taken off at a boiling point of 50° to 60° C.; according to analysis by gas chromatography, it contained 73.8% of Me$_2$HSiOEt. 376 g of distillate were obtained. (2.66 mols of Me$_2$HSiOEt or 75.9%, relative to Me$_2$Si(OEt)$_2$ employed).

It will be appreciated that the instant specification and examples are set forth by way of illustration and not limitation, and that various modifications and changes may be made without departing from the spirit and scope of the present invention.

What is claimed is:

1. A process for the preparation of a silane of the formula $$R_aSiH_b(OR')_{4-(a+b)}$$

wherein

R is optionally subsituted alkyl, alkenyl or aryl with up to 7 C atoms,

R' is alkyl with 1 to 4 C atoms, a and b each independently is 1, 2 or 3, and a+b is at most 4, comprising reacting an Si-H polysiloxane with a compound of the formula $$R_aSi(OR')_{4-a}$$

in the presence of a conventional redox-stable siloxane polymerization catalyst which favors the exchange reaction.

2. The process according to claim 1, wherein AlCl$_3$ is employed as the catalyst.

3. The process according to claim 2, wherein R and R' each independently is methyl, ethyl, vinyl or phenyl.

* * * * *